(12) United States Patent
Howell

(10) Patent No.: US 8,167,874 B2
(45) Date of Patent: May 1, 2012

(54) ASSEMBLY AND KIT FOR MARKING TUBAL OSTIA

(75) Inventor: Thomas G. Howell, Faribault, MN (US)

(73) Assignee: Mayo Foundation for Medical Education, Rochester, NY (US)

( * ) Notice: Subject to any disclaimer, the term of this patent is extended or adjusted under 35 U.S.C. 154(b) by 2051 days.

(21) Appl. No.: 11/184,197

(22) Filed: Jul. 19, 2005

(65) Prior Publication Data

US 2006/0015070 A1 Jan. 19, 2006

Related U.S. Application Data

(60) Provisional application No. 60/589,112, filed on Jul. 19, 2004.

(51) Int. Cl.
- *A61B 18/04* (2006.01)
- *A61B 18/02* (2006.01)
- *A61B 18/18* (2006.01)

(52) U.S. Cl. .......................... 606/32; 606/34

(58) Field of Classification Search .............. 606/1, 116, 606/32–50; 128/898
See application file for complete search history.

(56) References Cited

U.S. PATENT DOCUMENTS

| | | | | |
|---|---|---|---|---|
| 3,948,259 A | * | 4/1976 | Bolduc et al. | 128/831 |
| 4,245,623 A | * | 1/1981 | Erb | 128/831 |
| 5,147,353 A | * | 9/1992 | Everett | 606/15 |
| 5,273,527 A | * | 12/1993 | Schatz et al. | 604/43 |
| 5,527,331 A | * | 6/1996 | Kresch et al. | 606/170 |
| 5,571,098 A | * | 11/1996 | Domankevitz et al. | 606/15 |
| 5,935,137 A | * | 8/1999 | Saadat et al. | 606/135 |
| 5,954,715 A | * | 9/1999 | Harrington et al. | 606/28 |
| 6,165,492 A | * | 12/2000 | Neuwirth | 424/430 |
| 6,461,296 B1 | * | 10/2002 | Desai | 600/210 |
| 6,508,815 B1 | * | 1/2003 | Strul et al. | 606/34 |
| 6,526,979 B1 | * | 3/2003 | Nikolchev et al. | 128/830 |
| 6,634,361 B1 | | 10/2003 | Nikolchev et al. | |
| 6,709,667 B1 | | 3/2004 | Lowe et al. | |

OTHER PUBLICATIONS

R. Sabbah, Clinical Results on Feasibility and Compatibility of the Essure Sterilization Immediately Following NovaSure Endometrial Ablation, Aug. 2003, The Journal of the American Association of Gynecologic Laporoscopists, vol. 10, No. 3 Supplement, S49.*
Robert Finn, Essure safe in combo with endometrial ablation, Dec. 15, 2004, OB/GYN News. http://findarticles.com/p/articles/mi_m0CYD/is_24_39/ai_n8697311/.*
Corson et al., Fertility Control, 1995, Little Brown & Co, 2nd Edition, p. 365.*
Corson et al, "Fertility Control", 1994, Goldin Publishers, Second Edition, p. 365.*
"mark." http://www.merriam-webster.com/dictionary/mark. Merriam-Webster, 2011. Web. Sep. 7, 2011.*

* cited by examiner

*Primary Examiner* — Michael Peffley
*Assistant Examiner* — Ronald Hupczey, Jr.
(74) *Attorney, Agent, or Firm* — Quarles & Brady LLP

(57) ABSTRACT

A method, apparatus, and kit for marking the opening between the fallopian tube and the uterus (tubal ostia) are provided. A marking dye provided in a marking assembly including a fluid dispenser coupled to a catheter having an open end and a guide wire. The catheter is inserted into the uterus and to a position adjacent the tubal ostia. When properly inserted, the fluid dispenser is activated to cause fluid to flow through the catheter and to the wall of the uterus to provide a mark. Once the mark is provided, endometrial ablation process can be provided in the uterus. The marks can then be used to guide the insertion of tubal occlusion devices.

6 Claims, 6 Drawing Sheets

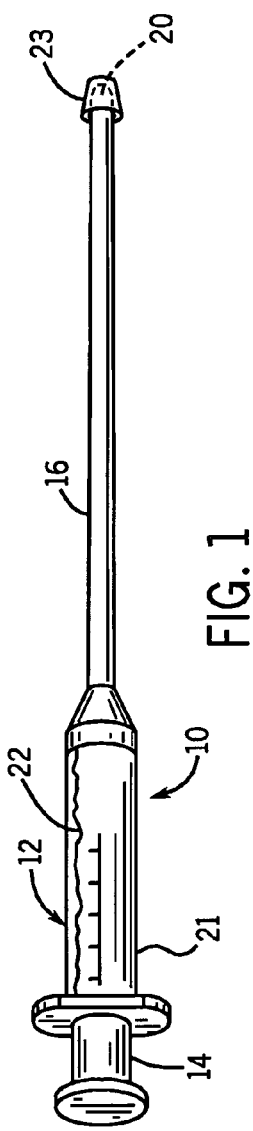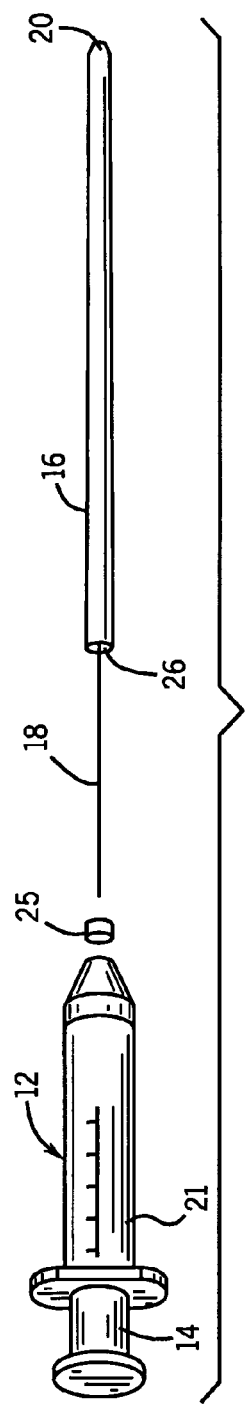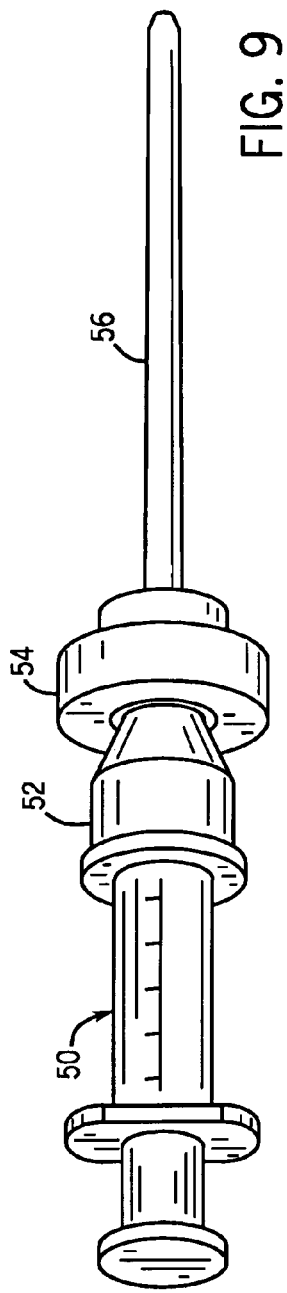

ASSEMBLY AND KIT FOR MARKING TUBAL OSTIA

CROSS-REFERENCE TO RELATED APPLICATION

The application claims priority to provisional application U.S. Ser. No. 60/589,112, filed Jul. 19, 2004.

STATEMENT REGARDING FEDERALLY SPONSORED RESEARCH OR DEVELOPMENT

--

BACKGROUND OF THE INVENTION

The present invention is related to methods and apparatuses for marking anatomical features for medical procedures, and is more particularly directed to a method, apparatus, and kit for marking openings between the fallopian tubes and the uterus (tubal ostia).

Menorrhagia is a disorder caused by hormonal disturbances, uterine fibroids, polyps, or overgrowth of the uterine lining, and which results in heavy or prolonged bleeding during the menstrual period. One treatment for menorrhagia is to remove the endometrium, or lining of the uterus, through a process called endometerial ablation. In endometrial ablation, the endometrium is burned away, vaporized, or otherwise ablated using a tool such as a heat generating or cryoablation device. After treatment, the endometrium heals by scarring, which usually reduces or prevents uterine bleeding.

Many women who are candidates for endometrial ablation are also of childbearing age, and in some cases it is therefore either advisable or desirable to prevent pregnancy after or in conjunction with the endometrial ablation. If sterilization is an appropriate choice for the patient, a selective tubal occlusion can be provided in conjunction with the ablation procedure. Selective tubal occlusion consists of placing occlusive devices at the openings of the fallopian tubes (the tubal ostia) to block the tubes from the uterus. Tubal occlusion is a non-surgical procedure that is desirable because it provides a significantly faster recovery time than, for example, surgical tubal ligation. Furthermore, tubal occlusion can be provided concurrently with the endometrial ablation procedure, thereby increasing efficiency and limiting the invasiveness of the procedures.

While it is desirable to combine endometrial ablation and tubal occlusion into a single procedure, however, the endometrial ablation procedure frequently results in debris which remains in the uterine cavity after ablation, and further changes the uterine wall such that the appearance of the uterus is significantly different after ablation than it had been prior to ablation. Therefore, it can be difficult to locate the tubal ostia after ablation, rendering a proper insertion of the tubal occlusion devices difficult or impossible.

BRIEF SUMMARY OF THE INVENTION

The present invention provides an assembly for marking tubal ostia. The assembly includes a marking dye, a fluid dispenser pre-filled with the marking dye, and a catheter sized and dimensioned for positioning in a uterus to extend to the tubal ostia. The catheter is coupled to the dispenser at a first end for receiving the dye from the dispenser and includes an opening at the second end for dispensing the dye. A guide wire is provided in the catheter for positioning the catheter adjacent the opening to allow marking the position of the tubal ostia with the marking dye.

The fluid dispenser can comprise a container which is formed integrally with the catheter, thereby limiting the number of components in the marking assembly and limiting the possibility of accidentally spilling the dye.

Alternatively, the catheter can be coupled to the fluid dispenser with an adapter suitable for this purpose, and a port seal can be coupled between the adapter and the catheter. The marking dye can be a methylene blue dye, and the catheter can be sized and dimensioned to be received in a hysteroscope.

The present invention also provides a method for marking tubal ostia. The method comprises filling a fluid dispenser with a biocompatible marking dye, coupling the dispenser to a catheter including an opening at each of a first and a second end and a guide wire, inserting the catheter into the uterus and positioning the first end of the catheter adjacent an opening between the fallopian tube and the uterus. When appropriately positioned, the fluid dispenser is activated to provide a flow of the marking dye through the catheter to mark the uterus wall adjacent the opening. This process can then be repeated to mark the second opening between the fallopian tube and the uterus.

After the marks are provided, an ablation device can be inserted into the uterus and activated to ablate the endometrium, and the first and second marks can be used to guide the insertion of a first and a second tubal occlusion device at the first and second tubal ostia.

In another aspect, the invention provides a kit for marking a tubal ostia including a fluid dispenser pre-filled with a methylene blue marking dye, and a catheter sized and dimensioned for positioning in a uterus and to extend substantially to the tubal ostia. The catheter is coupled to the fluid dispenser at a first end for receiving the methylene blue dye, and includes an open second end for dispensing the methylene blue dye. A guide wire is provided within the catheter such that the catheter is selectively positionable in the uterus with the second end adjacent the tubal ostia, and the fluid dispenser is selectively activated to cause the methylene dye to flow through the catheter to a wall of the uterus to mark the position of the tubal ostia. Instructions for marking the tubal ostia are included in the kit.

These and other aspects of the invention will become apparent from the following description. In the description, reference is made to the accompanying drawings which form a part thereof, and in which there is shown a preferred embodiment of the invention. Such embodiment does not necessarily represent the full scope of the invention reference is made therefore, to the claims herein for interpreting the scope of the invention.

BRIEF DESCRIPTION OF THE SEVERAL VIEWS OF THE DRAWINGS

FIG. 1 is a perspective view of a marking assembly constructed in accordance with the present invention.

FIG. 2 is an exploded view of the marking assembly of FIG. 1.

FIG. 9 is a perspective view of an alternate embodiment of the marking assembly of FIG. 1.

DETAILED DESCRIPTION OR THE PREFERRED EMBODIMENT

Figure 3:
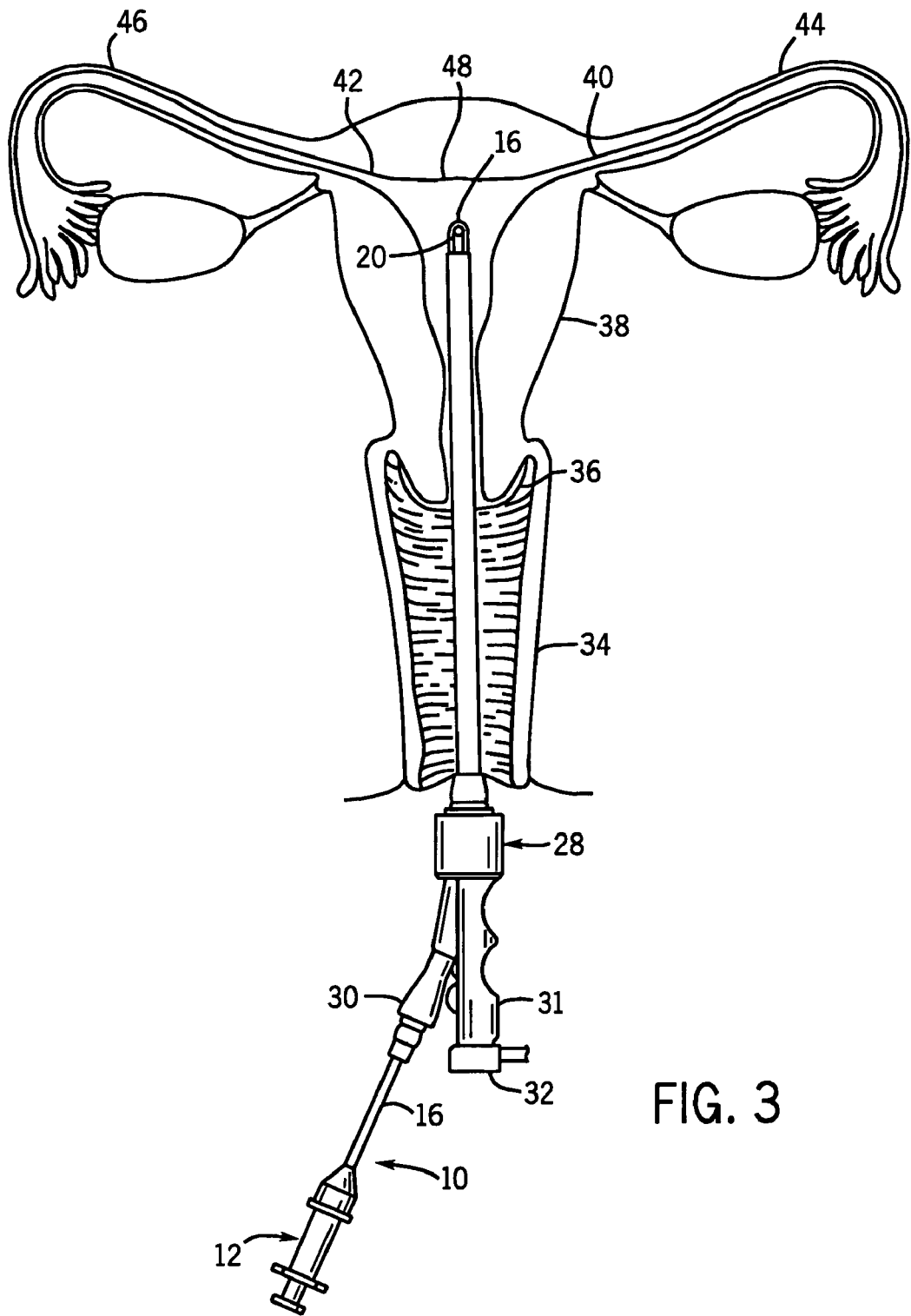
FIG. 3 is a view of the marking assembly of FIG. 1 as inserted in the uterus.

Referring now to the figures and more particular to FIG. 1, a marking assembly 10 useful for marking tubal ostia in the uterus is shown. The marking assembly 10 comprises a fluid dispenser 12 coupled to a catheter 16 having an opening at a distal end 20. A container 21 for receiving a marking dye 22 is provided in the fluid dispenser 12, and an actuator 14 is provided for forcing the marking dye 22 out of the container 21, into the catheter 16, and out of the opening at the distal end 20 of the catheter 16. A cap 23, which can be, for example, snap fit onto the catheter 16, can be provided to enclose the open end 20 to prevent accidental spillage of the marking dye 22 prior to use. The marking dye 22 is selected to be biocompatible and to provide marks that can be seen relatively easily when used to mark positions inside internal body cavities. Dyes which are relatively viscous and therefore easier to control when providing the mark are preferred. Although a number of marking dyes could be employed in the present invention, the marking dye 22 is preferably methylene blue, which provides marks in a color which can be easily seen, and also is more viscous than other types of surgical marking dyes. Other dyes suitable for surgical marking applications, such as indigo carmine, however, can also be used.

Referring now also to FIG. 2, an exploded view of the marking assembly 10 is shown. Internally, the catheter 16 includes a flexible guide wire 18 which stiffens the catheter 16 such that it can be more easily positioned adjacent the tubal ostia, as described below. The guide wire 18 can extend along the length of the catheter 16, substantially from a first open end 26 of the catheter 16 to the opposing open end 20, or in a portion of the catheter 16. A seal 25, such as a rubber gasket or O-ring can be provided between the catheter 16 and the fluid dispenser 12 to limit or prevent leaking of the dye 22 between these components. Although shown as separate components here, it will be apparent that the catheter 16 and container 21 could also be formed integrally as a single component. Other types of sealing devices, such as a threaded connection between the catheter and the fluid dispenser, could also be provided. The catheter 16 is sized and dimensioned to be received in a hysteroscope and to extend through the uterus to the tubal ostia, as described below. A catheter having a diameter of about 3 to 4 French and a length of about fifty centimeters, for example, is useful in this application.

Figure 4:
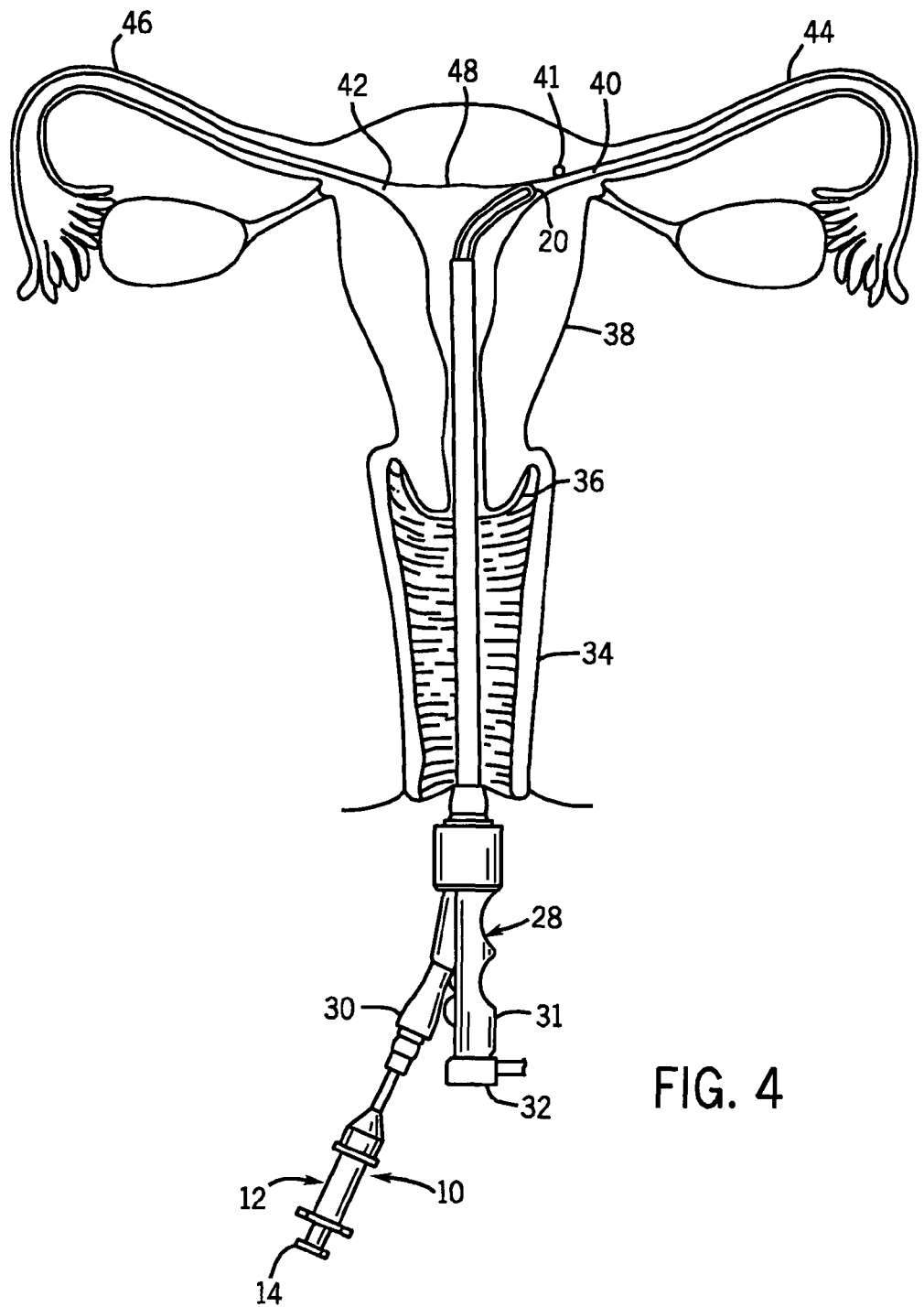
FIG. 4 is a view of the marking assembly of FIG. 1 as inserted in the uterus to mark a first tubal ostia.
Figure 5:
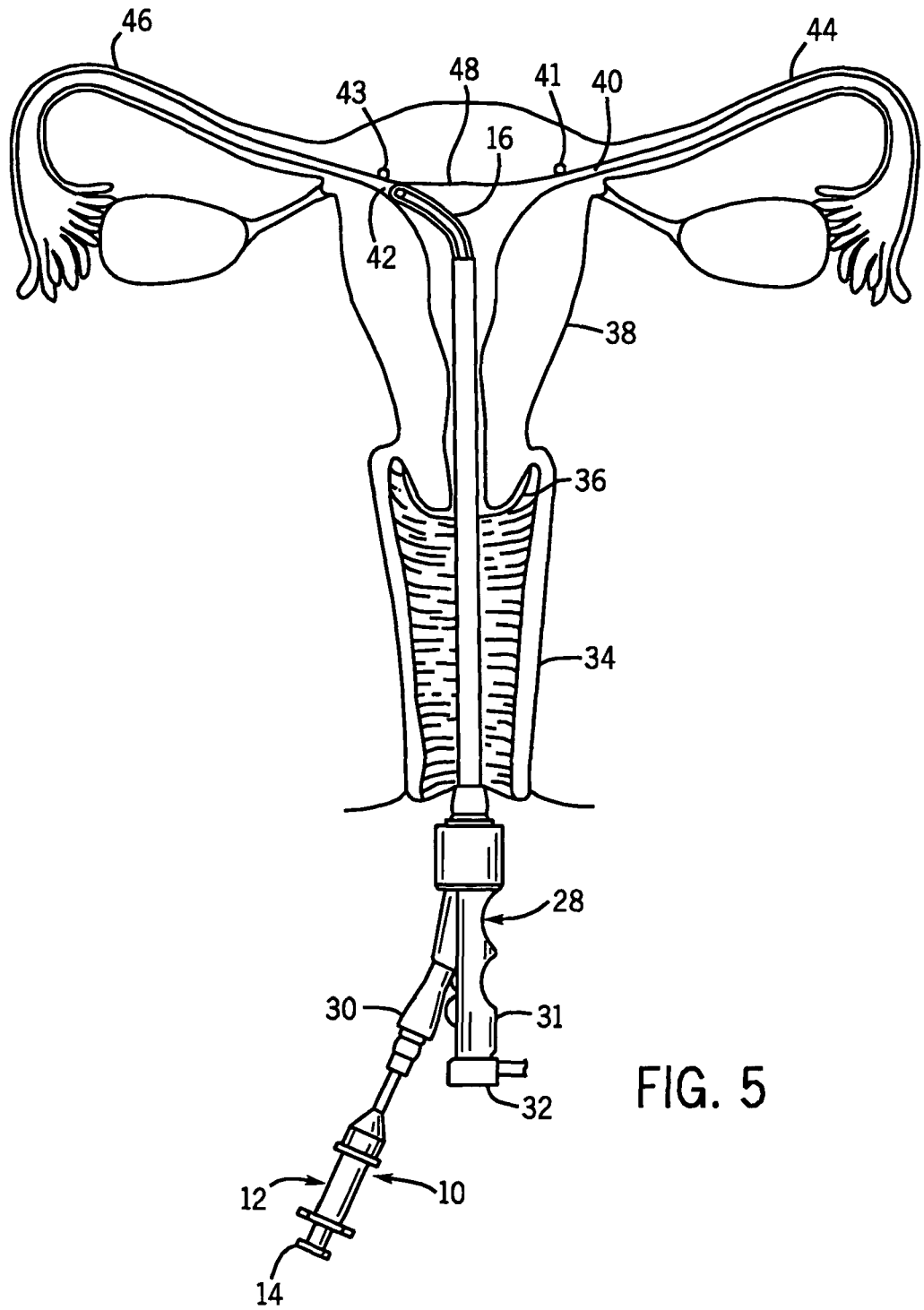
FIG. 5 is a view of the marking assembly of FIG. 1 as inserted in the uterus to mark a second tubal ostia.

Referring now to FIG. 3, the marking assembly 10 is shown as used to mark the tubal ostia 40 and 42 in the uterus 38. To provide the marking, the patient is sedated and anesthetized, typically with a local anesthetic placed into the cervix 36. The opening to the cervix 36, is then dilated using methods known to those of skill in the art. The catheter 16 of the marking device 10 is inserted into an operative channel 30 of an operative hysteroscope 28, including both a viewing channel 31 and an operative channel 30, until a tip of the catheter 16 is just visible outside of the operative channel 30. The hysteroscope 28 is then inserted into the vagina 34, and is extended through the cervix 36 and into the uterus 38. When the hysteroscope 28 is properly positioned, the practitioner performing the procedure views the inside of the uterus 38 through a scope 32 provided on the viewing channel 31 in the hyteroscope 28, and identifies the tubal ostia 40 located at the opening between the fallopian tube 44 and the uterus 38. The practitioner then positions the open end 20 of the catheter 16 adjacent the tubal ostia 40, as shown in FIG. 4. When appropriately positioned, the actuator 14 of the fluid dispenser 12 is activated forcing the marking dye 22 in the fluid dispenser 12 into the catheter 16, and out of the open end 20 such that the marking dye 22 is received on the wall of the uterus 38 adjacent the tubal ostia 40 to provide a mark 41 indicating the position of the tubal ostia 40. Referring now to FIG. 5, after the tubal ostia 40 is marked, the practitioner repositions the open end 20 of the catheter 16 to a position adjacent the second tubal ostia 42, where the fallopian tube 46 meets the uterus 38, and activates the actuator 14 to provide a second mark 43.

Figure 6:
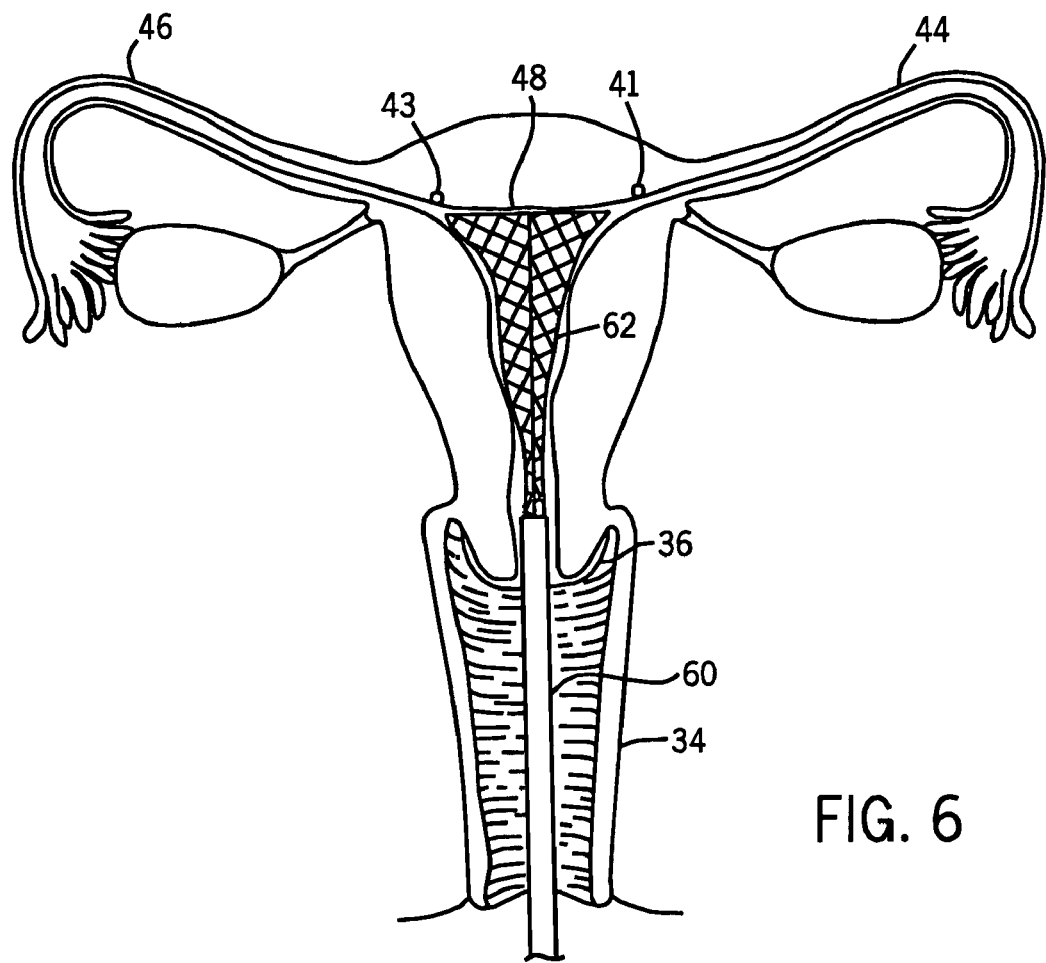
FIG. 6 is a view of an endometrial ablation device inserted in the uterus.

After the tubal ostia 40 and 42 are appropriately marked, menorrhagia can be treated using an endometrial ablation procedure. To perform the endometrial ablation, an ablation tool such as a resectoscope with a loop or rolling ball electrode, radiofrequency source, laser beam, high electric voltage tool, microwave tool, or cryoablation tool can be inserted into the operative channel 30 of the hysteroscope 28, and used to treat the endometrium. Referring now to FIG. 6, in a preferred embodiment, however, the hysteroscope 28 is removed after marking of the tubal ostia 40 and 42, and endometrial ablation is performed via controlled vaporization using the NovaSure™ system, which is commercially available from Cytyc Corp. of Boxborough, Mass. The NovaSure™ system includes a gold-plated mesh triangle 62 that is delivered into the uterus 38 via a slender tube 60 and, when appropriately positioned, is expanded into the uterus 38 of the patient. The shape of the mesh triangle 62 is configured to generally resemble the profile of the uterus 38, and after insertion, suction can be applied to bring the uterine cavity into close contact with the mesh 62. Once the mesh 62 is appropriately positioned, energy is delivered to the endometrial lining 48 via the mesh 62 for a period of typically one to two minutes. After the treatment, the mesh 62 is retracted and the tube 60 removed from the uterus 38.

Figure 7:
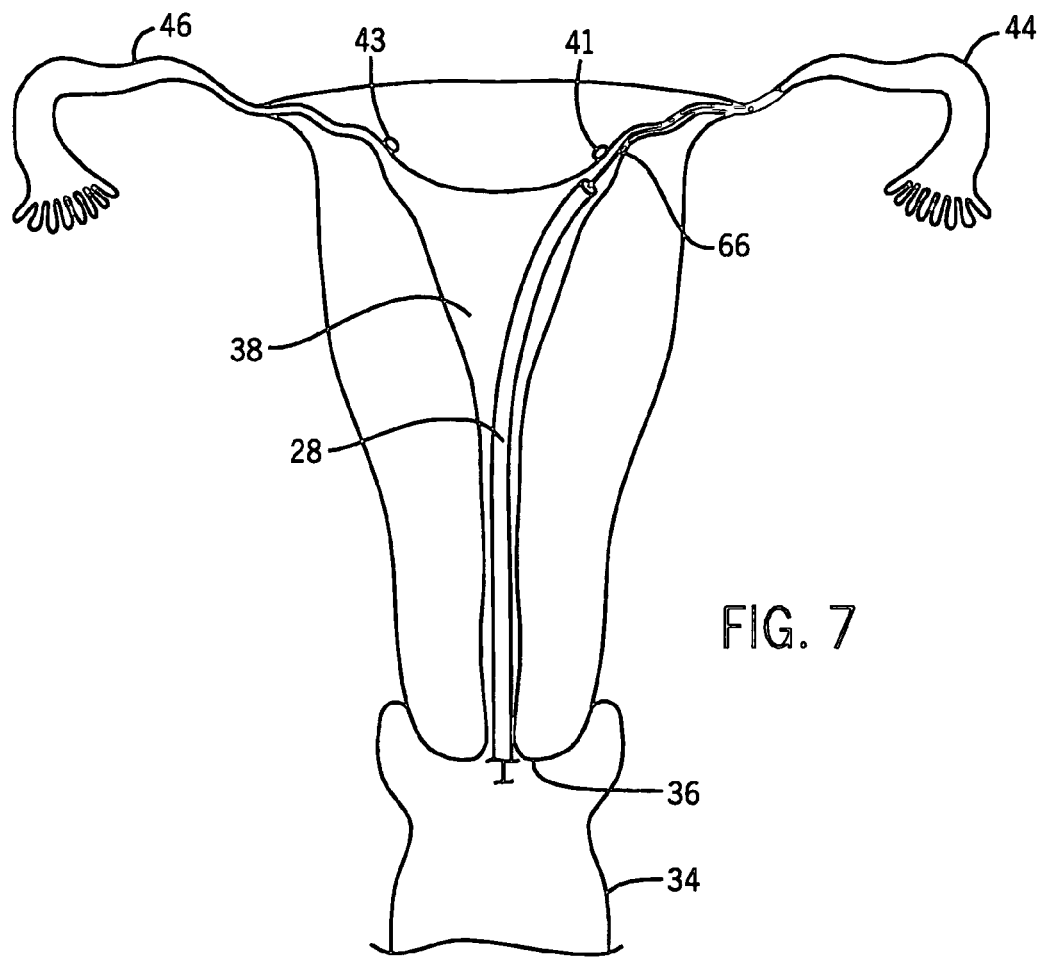
FIG. 7 is a view of a tubal occlusion device guided into the tubal ostia by the marks provided in FIGS. 4 and 5.
Figure 8:
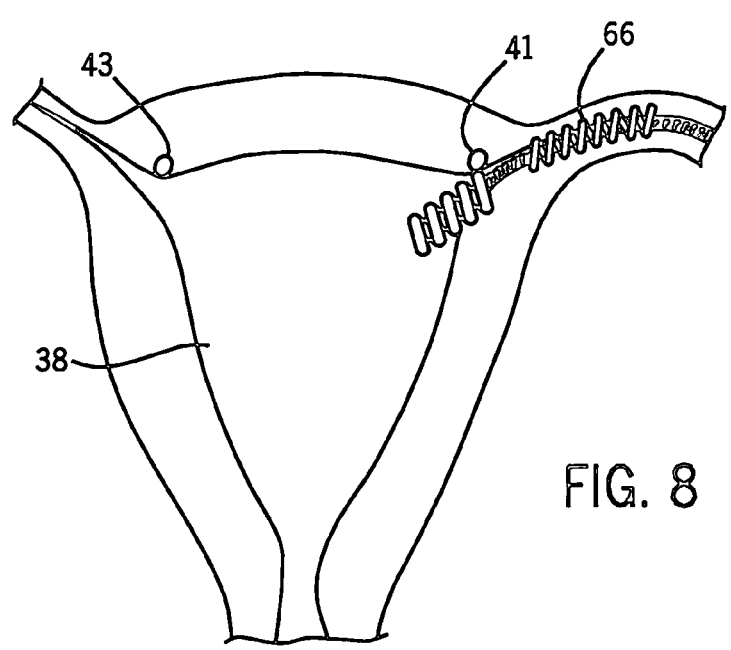
FIG. 8 is a view of the tubal occlusion device of FIG. 7 as inserted into the uterus.

Referring now to FIGS. 7 and 8, irrespective of the selected method of endometrial ablation, after the procedure is completed, the practitioner again examines the walls of the uterus 38 to locate the tubal ostia 40 and 42 for insertion of tubal occlusion devices 66. Here, the practitioner uses the scope 32 of the hysteroscope 28 to locate the tubal ostia 40 and 42 by identifying the marks 41 and 43 on the walls of the uterus 38. If the marks 41 and 43 are obscured or not visible, hysteroscopic grabbing forceps or a suction curette can be used to remove fragments or debris remaining from the ablation procedure. The tubal occlusion devices 66 can then be inserted into the operative channel 30 of the hysteroscope 28 and guided to the tubal ostia 40 and 42 using the marks 41 and 43 to appropriately position the devices. Again, while a number of tubal occlusion devices 66 and methods could be employed in the present application, one suitable occlusion device is the Essure™ device, commercially available from Conceptus, Inc. of Glen Furuta, Calif. The Essurem™ device is a transcervical fallopian tube occlusion device which, as shown in FIG. 8, is formed from a helical resilient structure that is inserted within the fallopian tube, as described more fully in U.S. Pat. Nos. 6,526,979 and 6,634361, which are hereby incorporated by reference herein for their description of these devices. One particular method and apparatus for inserting these devices using a hysteroscope is described in U.S. Pat. No. 6,709,667, which is also hereby incorporated by reference for its description of this method.

Referring now to FIG. 9, an alternate embodiment of a marking assembly 10 is shown. Here, the marking assembly 10 is constructed from a number of commercially-available components, and specifically comprises a syringe 50, a catheter adapter 52, a port seal 54, and an ureteral catheter 56. The syringe 50 is received in the catheter adapter 52 which is coupled to the port seal 54. The ureteral catheter 56 is received in the port seal 54, which clamps the catheter 56 to the syringe to limit leakage in the system. Although a number of commercially available products could be used in the assembly, in one embodiment, the assembly was successfully constructed using a three cubic centimeter syringe, an ureteral catheter adapter from CR Bard of Murray Hill, N.J., and a biopsy port seal capable of receiving catheters up to 6 French in diameter and commercially available from ACMI of Southborough, Mass. The catheter 56 is a 3 to 4 French ureteral catheter with an internal guide wire, also available from CR Bard, and having a length of approximately 50 cm. Although these components are suitable to the application, various other methods of connecting a syringe or other fluid dispensing device to a catheter will be apparent to those of skill in the art.

In a preferred embodiment of the invention, the marking assembly 10 is provided as a kit for marking tubal ostia. The kit includes a marking assembly 10 comprising a fluid dispenser 12 pre-filled with marking dye 22. Preferably, the fluid dispenser 12 is either pre-assembled to or formed integrally with a catheter 16 with an internal guide wire 18 to limit required assembly. As described above, a cap 23 can be provided on the catheter 16 to limit spillage, or, if the fluid dispenser 12 is provided separately from the catheter 16, on the fluid dispenser 12. Preventing spillage by pre-filling the dispenser 12, reducing required assembly of components, and providing caps or covers is particularly important when using methylene blue dye as the marking dye 22, as methylene dye is particularly prone to staining surfaces.

Although the kit preferably includes a pre-assembled marking device 10, the fluid dispenser 12 can be provided disassembled from the catheter 16, and adapters can be included for assembling the fluid dispenser 12 to the catheter 16, as described with reference to FIG. 9 above.

It should be understood that the methods described above are only exemplary and do not limit the scope of the invention, and that various modifications could be made by those skilled in the art that would fall under the scope of the invention. For example, various methods of combining a catheter and a fluid dispensing device will be apparent. Furthermore, while the dispenser is shown as having a specific actuator, squeeze bottles or other devices could also be used. Additionally, although the marking assembly has been shown and described for use in marking the tubal ostia for inserting tubal occlusion devices after endometrial ablation, it will be apparent that the marking assembly could also be used for marking various other locations in the uterus or other cavities, and used in conduction with other procedures. To apprise the public of the scope of this invention, the following claims are made:

I claim:

1. A method for marking tubal ostia, the method comprising the following steps:
    (a) providing a fluid dispenser with a biocompatible marking dye;
    (b) coupling a catheter including an opening at each of a first and a second end to an outlet of the fluid dispenser, wherein the first end is adjacent the fluid dispenser and the opposing end provides an open end at the opposing end of the catheter;
    (c) inserting the catheter into a uterus of a patient and positioning the open end of the catheter adjacent a tubal ostium; and
    (d) activating the fluid dispenser to provide a flow of the biocompatible marking dye through the catheter and through the open end of the catheter to provide a mark on the wall of the uterus indicating a position of the tubal ostium;
    (e) positioning the catheter adjacent a second tubal ostium; and
    (f) activating the fluid dispenser to dispense fluid on the wall of the uterus to provide a second mark indicating a position of the second tubal ostium;
    (g) inserting an ablation device into the uterus and ablating the endometrium; and
    (h) using the mark and the second mark to guide the insertion of a first and a second tubal occlusion device at the first and second tubal ostia.

2. The method as recited in claim 1, wherein step (c) further comprises the steps of:
    (i) inserting a hysteroscope including an operative channel into the uterus;
    (ii) inserting the catheter into the uterus through the operative channel; and
    (iii) monitoring the position of the catheter through the hysteroscope to position the catheter adjacent the tubal ostium.

3. The method as recited in claim 1, wherein step (h) comprises inserting a metal tubal occlusion coil.

4. The method as recited in claim 1, wherein step (g) comprises ablating the endometrium using a radiofrequency endometrial ablation.

5. The method as recited in claim 1, wherein step (a) comprises filling the dispensing device with a methylene blue dye.

6. The method as recited in claim 1, wherein step (h) further comprises the step of removing debris from the ablation from the uterus.

* * * * *

UNITED STATES PATENT AND TRADEMARK OFFICE
CERTIFICATE OF CORRECTION

| | |
|---|---|
| PATENT NO. | : 8,167,874 B2 |
| APPLICATION NO. | : 11/184197 |
| DATED | : May 1, 2012 |
| INVENTOR(S) | : Thomas G. Howell |

It is certified that error appears in the above-identified patent and that said Letters Patent is hereby corrected as shown below:

Column 2, line 49
"invention reference" should be --invention and reference--

Column 4, line 58
"Essurem" should be --Essure--

Column 6, line 2
"conduction" should be --conjunction--

Signed and Sealed this
Seventh Day of August, 2012

David J. Kappos
*Director of the United States Patent and Trademark Office*